United States Patent
Wu et al.

(10) Patent No.: US 8,445,742 B2
(45) Date of Patent: May 21, 2013

(54) WOUND DRESSING AND PROCESS FOR PRODUCING THE SAME AND USE THEREOF

(75) Inventors: Ta-Jen Wu, Sijhih (TW); Chih-Jen Li, Sijhih (TW); Chi-Sheng Chu, Sijhih (TW)

(73) Assignee: Coreleader Biotech Co., Ltd., Sijhih (TW)

( * ) Notice: Subject to any disclaimer, the term of this patent is extended or adjusted under 35 U.S.C. 154(b) by 352 days.

(21) Appl. No.: 12/787,986

(22) Filed: May 26, 2010

(65) Prior Publication Data

US 2011/0295172 A1  Dec. 1, 2011

(51) Int. Cl.
*A61F 13/00* (2006.01)
*B05D 7/00* (2006.01)
*D01D 5/06* (2006.01)

(52) U.S. Cl.
USPC ............... 602/45; 602/42; 602/48; 264/204; 427/2.31

(58) Field of Classification Search . 602/41–59; 19/145, 19/296; 427/2.31
See application file for complete search history.

(56) References Cited

U.S. PATENT DOCUMENTS

| | | | | |
|---|---|---|---|---|
| 2,951,047 | A * | 8/1960 | Lantos | 524/32 |
| 4,044,404 | A * | 8/1977 | Martin et al. | 623/1.54 |
| 4,399,035 | A * | 8/1983 | Nohmi et al. | 210/500.23 |
| 5,470,576 | A * | 11/1995 | Patel | 424/445 |
| 6,638,615 | B2 * | 10/2003 | Kobayashi et al. | 428/367 |

* cited by examiner

*Primary Examiner* — Kim M Lewis
(74) *Attorney, Agent, or Firm* — Shimokaji & Associates P.C.

(57) ABSTRACT

A process for producing a wound dressing was provided having steps of: spinning an aqueous stock containing natural polymeric materials into a spin formation solution to form a wet polymeric spin; immersing the wet polymeric fiber into a softening reagent to obtain a softened wet polymeric spin; immersing the softened wet polymeric spin into a volatile reagent to expelling moisture in the softened wet polymeric fiber to form a polymeric fiber; forming a non-woven fabric of the polymeric fiber; and treating the non-woven fabric of the polymeric fiber with a coating solution to form a porous coating on the polymeric fiber to obtain a wound dressing. A process for manufacturing a polymeric fiber is also provided. A wound dressing produced by the process is also provided.

19 Claims, 2 Drawing Sheets

WOUND DRESSING AND PROCESS FOR PRODUCING THE SAME AND USE THEREOF

BACKGROUND OF THE INVENTION

1. Field of the Invention

The present invention relates to a process for manufacturing a polymeric fiber and a process for producing a wound dressing composed of the polymeric fiber. The present invention also relates to the polymeric fiber and wound dressing produced by the method according to the present invention.

2. Description of the Prior Arts

Current wound dressings are composed of materials and with a form of gel, film or sponge. These dressings have been commercially available for a period of time; however, when considering their applications in some aspects, there are still existing problems due to their mechanical strength, absorption amount and absorbing rate. The most common structure of wound dressings in the field includes sponge-like and non-woven fabrics, wherein permeability of the non-woven fabrics is better than that of the sponge-like fabrics. Most of all, non-woven fabrics has a structure suitable for absorbing cells and allowing cells to proliferate. Furthermore, non-woven fabrics have fair softness and certain degree of mechanical strength and can be produced by continuous process so as to have benefits to reduce its cost.

Common wound dressing is usually made of recycled natural polymeric fiber. Current polymeric fiber is made by wet spinning with requirement for lyophilization of wet spins to form polymeric fibers. As known, lyophilization is energy-consuming. Moreover, for non-woven fabrics manufactured by wet-laid process, an additional lyophilization is required. For non-woven fabrics manufactured by needle punch, an additional needle punch machine is required. To summarize, conventional methods for manufacturing natural polymeric fiber or for producing non-woven fabrics as wound dressings in the field is energy consuming and requires extra expensive apparatuses.

To overcome the shortcomings of the conventional techniques for manufacturing fibers and fabrics composed thereof, the present invention provides a method for producing a polymeric fiber to mitigate or obviate the aforementioned problems.

SUMMARY OF THE INVENTION

The main objective of the invention is to provide a process for producing a wound dressing. The process in accordance with the present invention requires less drying means during procedures from manufacturing biocompatible polymeric fibers to form a wound dressing.

Accordingly, the present invention provides a process for manufacturing a polymeric fiber, which comprises steps of:
(i) spinning an aqueous dope containing natural polymeric materials into a spin formation solution to form a wet polymeric spin;
(ii) immersing the wet polymeric spin into a softening reagent to obtain a softened wet polymeric spin; and
(iii) immersing the softened wet polymeric spin into a volatile reagent to expelling moisture in the softened wet polymeric spin to form a polymeric fiber.

In another aspect, the present invention provides a process for producing a wound dressing, comprising steps of:
(i) obtaining a polymeric fiber according to the process as described above;
(ii) forming a non-woven fabric of the polymeric fiber; and
(iii) treating the non-woven fabric of the polymeric fiber with a coating solution to form a porous coating on the polymeric fiber to obtain a wound dressing.

In another aspect, the present invention provides a wound dressing, which is produced by the method in accordance with the present invention.

A wound dressing in accordance with the present invention comprises a non-woven fabric of polymeric fibers; and a porous coating on the non-woven fabric of the polymeric fibers.

The method in accordance with the present invention enables wound dressings to be prepared in a large-scale production without tedious steps for drying fibers or fabrics composed of said fibers. Therefore, the method and the wound dressing in accordance with the present invention have increased economic value. The wound dressing in accordance with the present invention is also proven to have improved effects on agglutination and wound healing and show no stimulus to skin of animals.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
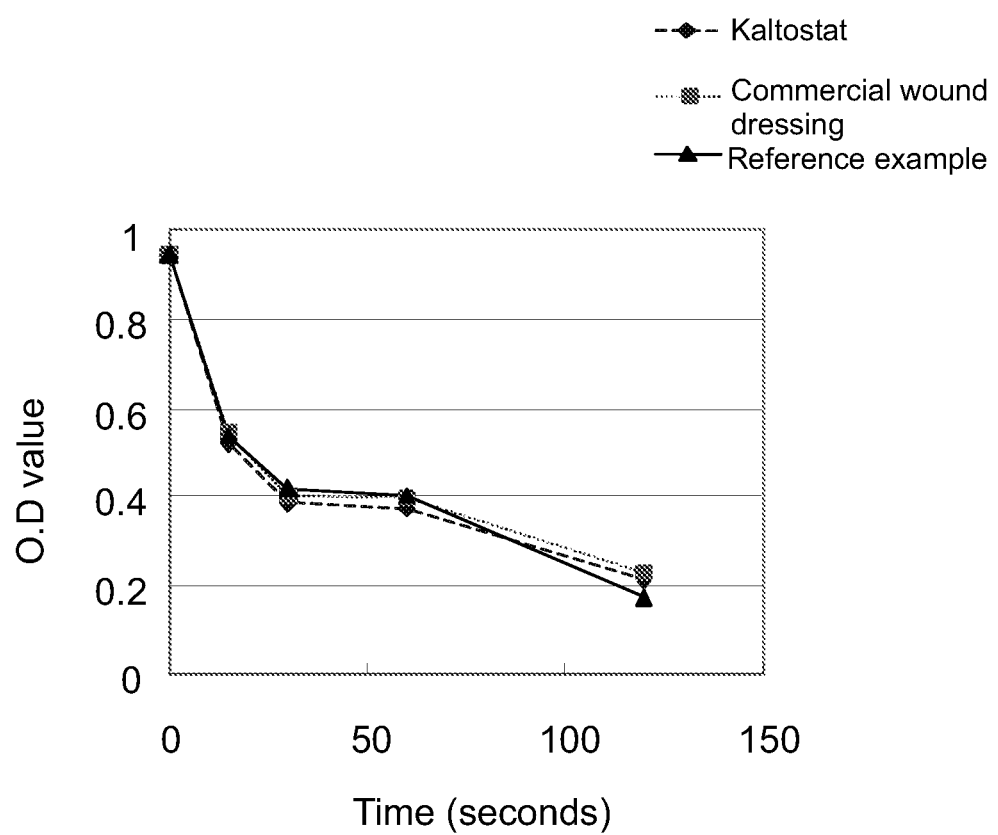
FIG. 1 illustrates comparison between effect on agglutination of a commercial dressing made by alginate and wound dressing obtained from the wet-laid example made by alginate.

A process for manufacturing a polymeric fiber, comprising steps of:
(i) spinning an aqueous stock containing natural polymeric materials into a spin formation solution to form a wet polymeric spin;
(ii) immersing the wet polymeric fiber into a softening reagent to obtain a softened wet polymeric spin; and
(iii) immersing the softened wet polymeric spin into a volatile reagent to expelling moisture in the softened wet polymeric fiber to form a polymeric fiber.

A process for producing a wound dressing in accordance with the present invention comprises steps of:
(i) obtaining a polymeric fiber according to the process for manufacturing a polymeric fiber according to the present invention;
(ii) forming a non-woven fabric of the polymeric fiber; and
(iii) treating the non-woven fabric of the polymeric fiber with a coating solution to form a porous coating on the polymeric fiber to obtain a wound dressing.

According to the present invention, the step of forming a non-woven fabric of the polymeric fiber includes any known techniques in the art for preparing non-woven fabrics from fibers with appropriate length. For examples, non-woven fabric of the polymeric fiber may be formed by carding and wet-laid.

In a preferred embodiment, the step of forming a non-woven fabric of the polymeric fiber includes: carding polymeric fibers to obtain a non-woven fabric of the polymeric fiber.

In a preferred embodiment, a step of depositing polymeric fibers onto a collecting belt in a uniform random manner is performed and followed by bonding the polymeric fibers.

In a preferred embodiment, the step of forming a non-woven fabric of the polymeric fiber includes: cutting the polymeric fiber into short fibers; and laying the short fibers in water to obtain a wet non-woven fabric.

According to the present invention, the natural polymeric materials include materials selected from the group consisting of: chitosan, alginate and a combination thereof.

In a preferred example in accordance with the present invention, the aqueous stock containing natural polymeric materials is an aqueous solution containing chitosan at a concentration between 3 and 10% w/w; and the spin formation solution contains at least one alkaline compound at a concentration between 3 and 10% w/w.

In another preferred example in accordance with the present invention, the aqueous stock containing natural polymeric materials is an aqueous solution containing sodium alginate at a concentration between 3 and 10% w/w; and the spin formation solution contains divalent cation at a concentration between 3 and 10% w/w.

According to the present invention, the divalent cation includes, but not limited to calcium ion.

According to the present invention, the softening reagent allows a wet polymeric spin to keep a proper flexibility.

According to the present invention, the softening reagent includes, but not limited to: glycerol, polysorbate and derivatives thereof, such as Tween-20, Tween-60, Tween-80 and Span-80. Preferably, the softening reagent is selected from the group consisting of: a glycerol solution at a concentration between 0.1 and 25% (w/w) and a polysorbate solution at a concentration between 0.1 and 10% (w/w).

According to the present invention, immersing into a volatile reagent includes immersing the softened wet polymeric spin into reagent selected from the group consisting of: low-carbon alcohol, low-carbon ketone and low-carbon ether.

The low-carbon alcohol refers to methanol, ethanol, propanol, butanol, pentanol or hexanol. Low-carbon ketone refers to $C_1$ to $C_6$ ketone. Low-carbon ether refers to $C_2$ to $C_6$ ether.

In a preferred embodiment of the method in accordance to the present invention, the step of treating the non-woven fabric of the polymeric fiber with a natural polymer solution could be a step for an inter-fiber bonding to enhance adhesion between fibers and includes:

spraying a coating solution onto the non-woven fabric to form a non-woven fabric with a porous coating on the polymeric fiber; and drying the non-woven fabric with the porous coating to obtain the wound dressing.

Preferably, the step of spraying a coating solution onto the non-woven fabric includes spraying the coating solution at a speed between 10 and 100 mL per minute.

Preferably, the step of drying the non-woven fabric with the porous coating includes drying the non-woven fabric with the porous coating at a temperature between 35 and 85° C. to obtain the wound dressing.

According to the present invention, the coating solution contains at least one substance selected from the group consisting of: gelatin, collagen, sodium alginate, chitosan and hyaluronan.

According to the method of the present invention, a wound dressing is produced by steps as described above and comprises a non-woven fabric of polymeric fibers; and a porous coating on the non-woven fabric of the polymeric fibers.

The term "non-woven fabric of the polymeric fibers" as used herein refers to a fabric made of polymeric fibers by any known process in the art for preparing non-woven fabric from the polymeric fiber obtained in accordance with the present invention.

The process for producing a polymeric fiber comprises steps of:

spinning an aqueous stock containing natural polymeric materials into a spin formation solution to form a wet polymeric spin;

immersing the wet polymeric fiber into a softening reagent to obtain a softened wet polymeric spin; and immersing the softened wet polymeric spin into a volatile reagent to expelling moisture in the softened wet polymeric fiber to form a polymeric fiber.

According to the present invention, the natural polymeric materials include materials selected from the group consisting of: chitosan, alginate and a combination thereof; and the polymeric fibers are selected from chitosan fibers and alginate fibers.

The present invention is further illustrated by the following examples; it should be understood that the examples and embodiments described herein are for illustrative purposes only and should not be construed as limiting the embodiments set forth herein.

Reference Example Preparation of Chitosan Composite Fiber with Conventional Method An alkaline solution containing at least alkaline compound was prepared. A chitosan solution containing 5% w/w chitosan was prepared and extruded into the alkaline solution to form a wet chitosan spin. The wet chitosan spin was lyophilized to obtain a chitosan fiber. A certain amount of said chitosan fiber was cut into 2 to 3 cm and dispersed in water by high speed of blender and formed a non-woven chitosan fabric by a wet-laid process, followed by lyophilizing the same to dry. In the present reference example, each of the two lyophilization steps lasted for 2 to 3 days, which is vastly time- and electricity-consuming.

Example 1

Preparation of Chitosan Composite Fiber

A chitosan solution containing 5% w/w chitosan (M.W. about 300 k dalton) was prepared. An alkaline solution containing 5% sodium hydroxide was prepared. The chitosan solution was extruded into the alkaline solution to form a wet chitosan spin. The wet chitosan spin was then immersed in 2% Tween-20 for 5 minutes and subjected to solvent exchange by sequentially sinking in 50%, 60% and 70% ethanol in water each for 5 minutes. The wet chitosan spin was then subjected to a padder to repel extra solvent therein and dried at 60° C. for 2 hours to obtain a chitosan composite fiber. The whole process for preparing the chitosan composite took 4 hours.

Example 2

Preparation of Alginate Composite Fiber

An alginate solution containing 5% w/w sodium alginate was prepared. A salt solution containing 5% calcium chloride was prepared. The alginate solution was extruded into the salt solution to form a wet alginate spin. The wet alginate spin was then immersed in 2% Tween-20 for 5 minutes and subjected to solvent exchange by sequentially sinking in 50%, 60% and 70% ethanol in water each for 5 minutes. The wet alginate was then subjected to a padder to repel extra solvent therein and dried at 60° C. for 2 hours to obtain an alginate composite fiber. The whole process for preparing the alginate composite fiber took 4 hours.

Example 3

Preparation of Composite Wound Dressings with Porous Biopolymer Materials

The obtained chitosan composite fibers were respectively cut into short fibers at an appropriate length, processed by carding machine, sprayed with 0.5% sodium alginate solution on a collecting roller at an amount per time unit of 50 mL/min for fiber bonding and then dried to form a porous biopolymer material containing sodium alginate. Various solutions, especially collagen, gelatin or hyaluronan, may be used as replacements for the sodium alginate solution to form various porous biopolymer materials.

The obtained porous biopolymer materials formed as a web was subjected to a padder to expel liquid therein and dried at 60° C. for 2 hours to obtain a non-woven and porous composite wound dressing, including chitosan composite wound dressing, alginate composite wound dressing and etc. The chitosan composite wound dressing was used in the following examples.

Example 4

Determination of Weight Per Unit Area of Composite Wound Dressings

The obtained chitosan composite wound dressing was cut into pieces, each of area of 10×10 cm$^2$, and weighted by electronic scale. The weight per unit area of each wound dressing was calculated and shown in Table 1. The average weight per unit area was 0.0146 g/cm$^2$, equivalent to 146 g/m$^2$.

TABLE 1 weight per unit area of chitosan composite wound dressings each with an area of 100 cm$^2$

| Sample no. | | | | | | | | | |
|---|---|---|---|---|---|---|---|---|---|
| | 1 | 2 | 3 | 4 | 5 | 6 | 7 | 8 | 9 |
| Weight (g) | 1.51 | 1.43 | 1.52 | 1.43 | 1.44 | 1.46 | 1.49 | 1.43 | 1.43 |

Example 5

Absorption Test of Composite Wound Dressings

1. Experimental Materials and Apparatus

The chitosan composite wound dressing obtained by the method as described in Example 3 and deionized water and saline with various salt concentration were used in the present example.

2. Experimental Method

The experimental method used in the present invention includes the steps of:
  a. weighting a wound dressing of a determined size by electronic scale to obtain a original weight;
  b. immersing the wound dressing in deionized water and saline with various salt concentration as indicated below for 8 hours; and
  c. taking out and weighting the immersed wound dressing out to obtain a final weight.

A difference between the final weight and the original weight and a ratio of absorption were respectively calculated. The results were shown in Table 2. The absorptions of all wound dressings were increased with salt concentration and greater than 100%.

TABLE 2

Results of absorption test

| | Salt concentration (%) | | | |
|---|---|---|---|---|
| | 0 | 0.25 | 0.5 | 1 |
| Absorption (%) | 707.79 | 522.03 | 439.77 | 402.29 |

Example 6

Agglutination Test of Composite Wound Dressings

1. Experimental Materials and Apparatus

The chitosan composite wound dressing obtained by the method as described in Example 3, the wound dressing obtained by the method as described in the reference example, saline, whole blood from volunteer donor and ELISA kit (BioAssay Systems QuantiChrom Hemoglobin Assay kit) were used in the present example. A commercial dressing (Kaltostat®)(ConvaTec, USA) was used as control in the present example.

2. Experimental Method

The experimental method used in the present invention includes the steps of:
  a. drawing whole blood from a volunteer donor and exposing the whole blood under oxygen for 30 minutes;
  b. mixing 0.1 g chitosan composite wound dressings with 30 μL whole blood; and transferring chitosan composite wound dressings into saline at 30, 60, 90 and 120 seconds after initial of mixing and shaking for 4 minutes; and
  c. aspiring supernatant of said shaken saline for measuring of absorbance at a wavelength of 540 nm by ELISA, wherein reference wavelength is 650 nm.

As shown in FIG. 1, effect on agglutination of a commercial dressing and wound dressing obtained from the wet-spin method as described in the reference example were compared. The later has a similar effect to the commercial dressing. Diamond and square respectively represented commercial dressings. Square and Triangle represented two independent wound dressings obtained by the wet-spin method as described in the reference example. Based on the results, the wound dressing obtained by wet-laid method has similar effect as commercial wound dressing that is made by needle punch method.

Figure 2:
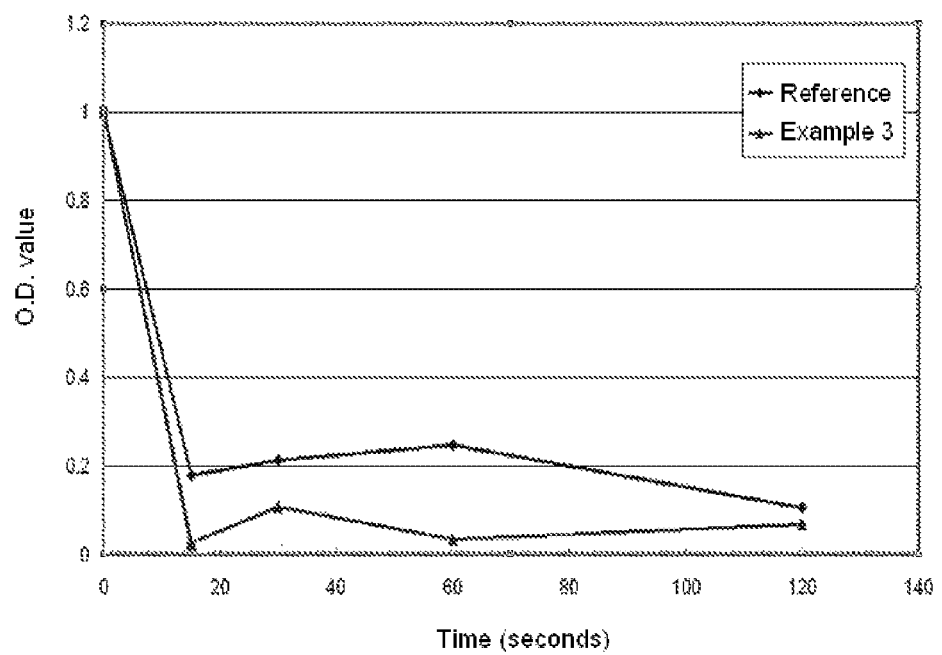
FIG. 2 illustrates effect of an obtained wound dressing in accordance to the present invention on agglutination and wound dressing obtained from the wet-laid example made by chitosan.

As shown in FIG. 2, an obtained wound dressing in accordance to the present invention was proven to have positive effects on promoting agglutination. Triangle represented dressing obtained from Example 3. Diamond represented control dressing obtained from the reference example. Based on the results, the wound dressing in accordance with the present invention has improved positive effect on agglutination.

Example 7

Determination of Wound Healing Effect of Composite Wound Dressings

1. Experimental Materials and Apparatus

The chitosan composite wound dressing obtained by the method as described in Example 3, the chitosan composite wound dressing without spraying of sodium alginate obtained by the method as described in the reference example, white rat (Wistar rat) and microscope were used in the present example.

2. Experimental Method The experimental method used in the present invention includes the steps of:

a. intramuscularly injecting 0.001 mL/g anesthetic into the rat;

b. shaving two lateral regions of abdomen of the rat and fully dehairing with hair remover as experimental regions;

c. sterilizing the experimental regions with iodine and creating two wounds of area of 4 square centimeter (2×2 $cm^2$);

d. covering the wounds with chitosan composite wound dressing and control dressing respectively;

e. observing and recording changes of the wounds including attachment of dressings and wounds, amount of fluid excreted from wounds, infection of periphery of wounds and size of wounds by digital camera.

3. Results

A. Measurement of Area of Wound

Area of wounds applied with dressing prepared by method as described in the reference example and Example 3 were shown in Table 3.

TABLE 3

Comparison between healing of wound applied with chitosan composite wound dressing and with control

| Week | Length of wound Control[a] | Length of wound Example 3[b] | Width of wound control | Width of wound Example 3 | Area of wound Control | Area of wound Example 3 |
|---|---|---|---|---|---|---|
| 0 | 2 | 2 | 2 | 2 | 4 | 4 |
| 1 | 1.8 | 1.5 | 1.8 | 1.7 | 3.24 | 2.55 |
| 2 | 1.5 | 1.6 | 0.4 | 0.7 | 0.6 | 1.12 |
| 3 (1st rat) | 1.9 | 1.2 | 0.3 | 0.5 | 0.57 | 0.6 |
| 3 (2nd rat) | 1.5 | 0.7 | 0.2 | 0.4 | 0.3 | 0.28 |
| 3 (3rd rat) | 1.1 | 0.6 | 0.3 | 0.6 | 0.55 | 0.36 |

[a]dressing obtained as described in the reference example
[b]chitosan composite wound dressing obtained as described in Example 3.

As shown in Table 3, chitosan composite wound dressing and control has a similar effect on wound healing. Wound that is applied with obtained as described in the reference example recovered to form an elongated callus. Wound that is applied with chitosan composite wound dressing obtained as described in Example 3 recovered to form an annular callus. The dressings were not adhered to the wounds and could be easily removed from the wounds.

Example 8

Tests for In Vitro Cytotoxicity of the Composite Wound Dressings

1. Experimental Materials and Apparatus

The chitosan composite wound dressing obtained by the method as described in Example 3, L929 mouse connective tissue cell line and fluorescence microscope were used in the present example (The Olympus FSX100 Bio Imaging Navigator all-in-one microscope).

2. Experimental Method

The test followed the standard protocol, ANSI/AAMI/ISO 10993-5:1999, named "Test for in vitro cytotoxicity of medical devices". L929 cells culture in culture medium were used as negative control group. L929 cells treated with PE film were uses as blank. L929 cells treated with phenol were used as positive control group.

Harvested cells from negative control group, blank (reagent only), positive control group and experimental group (the chitosan composite wound dressing obtain in Example 3) were counted by trypan blue staining. As shown in Table 3, the chitosan composite wound dressing obtained in Example 3 would not cause death of mouse fibroblast cells, indicating that the chitosan composite wound in accordance with the present invention has no cytotoxicity.

TABLE 3

Results of test for cytotoxicity of the chitosan composite wound dressing

| Group | Average of cell number (cells/mL) |
|---|---|
| Negative control group | $1.27 \times 10^6$ |
| Blank | $1.3 \times 10^6$ |
| Positive control group | $1.67 \times 10^4$ |
| Experimental group | $1.11 \times 10^6$ |

Example 9

Test for Intradermal Irritation of the Composite Wound Dressing

1. Experimental Materials

The chitosan composite wound dressing obtained by the method as described in Example 3, saline and New Zealand white rabbits were used in the present example.

2. Experimental Method

The experimental method used in the present invention includes the below-listed steps.

a. Samples were prepared by the standard protocol, ANSI/AAMI/ISO 10993-12:2007, named "Biological evaluation of medical devices—Part 12: Sample preparation and reference materials". Saline and cottonseed oil were used as extracting reagents. The extraction ratio was 6 $cm^2$/mL. Analytes were immersed in extracting reagent at a ratio as indicated at a speed of 100 rpm at 37° C. for 72 hours. Furthermore, extracting reagent only subjected to the same procedure was used as blank.

b. Dorsal hairs of two rabbits for each group were removed 18 to 24 hours before the test, resulting in an exposed skin area of 15 cm×10 cm. The skin area was checked for no damage before test by eyes.

c. Saline extract of analyte was intradermally injected into the rabbits at five front positions of a left portion of the skin area of each rabbit. Meanwhile, saline blank was intradermally injected into the rabbits at five rear positions of the left portion as control. Cottonseed oil extract and its blank was injected into the rabbits as described above. For each position, injected amount for each position was 0.2 mL d. Responses including erythema and edema of each experimental position and each control position were recorded at 24, 48 and 72 hours after injection according to score system for intradermal response as shown in Table 4.

TABLE 4

Score system for intradermal response

| Response | score |
|---|---|
| formation of erythema and callus | |
| no erythema | 0 |
| mild erythema | 1 |
| clear erythema | 2 |
| moderate erythema | 3 |
| severe erythema to form callus to hard to evaluate | 4 |
| Edema | |
| no edema | 0 |
| mild edema | 1 |
| clear edema | 2 |
| moderate edema | 3 |
| severe edema | 4 |
| Maximal score | 8 |

Scores of each experimental position and each control position at 24, 48 and 72 hours after injection were as shown in Table 5. The chitosan composite wound dressing in accordance with the present invention induced no irritating effect on animal skin.

TABLE 5

Scores of rabbit intradermal response

| | Score of response (erythema/edema) | | | |
|---|---|---|---|---|
| | Experimental position | | Control position | |
| Time (hour) | saline | cottonseed oil | saline | cottonseed oil |
| 1 | 0/0 | 0/0 | 0/0 | 0/0 |
| 24 | 0/0 | 0/0 | 0/0 | 0/0 |
| 48 | 0/0 | 0/0 | 0/0 | 0/0 |
| 72 | 0/0 | 0/0 | 0/0 | 0/0 |

Example 10

Test for Hypersensitivity of the Composite Wound Dressing

1. Experimental Materials and Apparatus

The chitosan composite wound dressing obtained by the method as described in Example 3, saline and male guinea pig were used in the present example.

2. Experimental Method

The experimental method used in the present invention includes the below-listed steps.

a. Samples were prepared by the standard protocol, ANSI/AAMI/ISO 10993-12:2007. Saline was used as extraction reagent. The extraction ratio was 3 cm²/mL. Analytes were immersed in the extracting reagent at a ratio as indicated at a speed of 100 rpm at 37° C. for 72 hours. Furthermore, extracting reagent only subjected to the same procedure was used as blank.

b. Guinea pigs were randomized into an experimental group of 10 and a control group of 5 before the test.

c. Hairs at shoulder blades of guinea pigs were removed 18 to 27 hours before the test as an experimental portion, resulting in an exposed skin area of 5 cm×7 cm. The skin area was checked for no damage before test by eyes.

d. Saline extract and saline were intradermally injected into two lateral sides of the skin area each at an amount of 0.1 mL one day before the test.

e. Hair grown at the experiment portion was removed again to expose a skin area, and the skin area was applied with 10% sodium dodecyl-sulfonate in vaseline 6 days after the test.

f. 0.5 mL extract of the analyte or blank was dropped on and fully absorbed by a 2 cm×4 cm swab. The swab was attached to the skin area of the experimental group or the control group for 48 hours and taken off.

g. After the swab was removed, the experimental portion of each guinea pig was evaluated according to a score system as shown in Table 6.

TABLE 6

Standard of Magnusson and Kligman test

| Response to swab test | score |
|---|---|
| no visible changes | 0 |
| discrete or patchy erythema | 1 |
| moderate and confluent erythema | 2 |
| Severe erythema and edema | 3 |

Scores of each experimental portion of experimental group and control group at 24, 48 and 72 hours after swab test showed no visible changes. The chitosan composite wound dressing in accordance with the present invention has no irritating effect on animal skin by the test for hypersensitivity.

Even though numerous characteristics and advantages of the present invention have been set forth in the foregoing description, together with details of features of the invention, the disclosure is illustrative only. Changes may be made in the details within the principles of the invention to the full extent indicated by the broad general meaning of the terms in which the appended claims are expressed.

What is claimed is:

1. A process for manufacturing a polymeric fiber, comprising steps of:
  (i) spinning an aqueous dope containing natural polymeric materials into a spin formation solution to form a wet polymeric spin;
  (ii) immersing the wet polymeric spin into a softening reagent to obtain a softened wet polymeric spin; and
  (iii) immersing the softened wet polymeric spin into a volatile reagent to expel moisture in the softened wet polymeric spin to form a polymeric fiber.

2. The process for manufacturing a polymeric fiber of claim 1, wherein the natural polymeric materials include materials selected from the group consisting of: chitosan, alginate and a combination thereof.

3. The process for manufacturing a polymeric fiber of claim 1, wherein the aqueous dope containing natural polymeric materials is an aqueous solution containing chitosan at a concentration between 3 and 10% (w/w); and the spin formation solution contains at least one alkaline compound at a concentration between 3 and 10% (w/w).

4. The process for manufacturing a polymeric fiber of claim 1, wherein the aqueous dope containing natural polymeric materials is an aqueous solution containing sodium alginate at a concentration between 3 and 10% (w/w); and the spin formation solution contains divalent cation at a concentration between 3 and 10% (w/w).

5. The process for manufacturing a polymeric fiber of claim 1, wherein the softening reagent is selected from the group consisting of: a glycerol solution at a concentration between 0.1 and 25% (w/w) and a polysorbate solution at a concentration between 0.1 and 10% (w/w).

6. The process for manufacturing a polymeric fiber of claim 2, wherein the softening reagent is selected from the group consisting of: a glycerol solution at a concentration between 0.1 and 25% (w/w) and a polysorbate solution at a concentration between 0.1 and 10% (w/w).

7. The process for manufacturing a polymeric fiber of claim 1, wherein the volatile reagent is selected from the group consisting of:
low-carbon alcohol, low-carbon ketone and low-carbon ether.

8. The process for manufacturing a polymeric fiber of claim 2, wherein the volatile reagent is selected from the group consisting of:
low-carbon alcohol, low-carbon ketone and low-carbon ether.

9. The process for manufacturing a polymeric fiber of claim 5, wherein the volatile reagent is selected from the group consisting of:
low-carbon alcohol, low-carbon ketone and low-carbon ether.

10. A process for producing a wound dressing, comprising steps of:
(i) spinning an aqueous dope containing natural polymeric materials into a spin formation solution to form a wet polymeric spin;
immersing the wet polymeric spin into a softening reagent to obtain a softened wet polymeric spin; and
immersing the softened wet polymeric spin into a volatile reagent to expelling expel moisture in the softened wet polymeric spin to form a polymeric fiber;
(ii) forming a non-woven fabric of the polymeric fiber; and
(iii) treating the non-woven fabric of the polymeric fiber with a coating solution to form a porous coating on the polymeric fiber to obtain a wound dressing.

11. The process for producing a wound dressing of claim 10, wherein the step of treating the non-woven fabric of the polymeric fiber with a coating solution includes:
spraying a coating solution onto the non-woven fabric to form a non-woven fabric with a porous coating on the polymeric fiber; and
drying the non-woven fabric with the porous coating to obtain the wound dressing.

12. The process for producing a wound dressing of claim 11, wherein the step of spraying a coating solution onto the non-woven fabric includes spraying the coating solution at a speed between 10 and 100 mL per minute.

13. The process for producing a wound dressing of claim 11, wherein the step of drying the non-woven fabric with the porous coating includes drying the non-woven fabric with the porous coating at a temperature between 35 and 85° C. to obtain the wound dressing.

14. The process for producing a wound dressing of claim 11, wherein the coating solution contains at least one substance selected from the group consisting of: gelatin, collagen, sodium alginate, chitosan and hyaluronan.

15. A wound dressing, which is produced by the method according to claim 10.

16. A wound dressing, which is produced by the method according to claim 11.

17. A wound dressing, which is produced by the method according to claim 12.

18. A wound dressing, which is produced by the method according to claim 13.

19. A wound dressing, which is produced by the method according to claim 14.

* * * * *